United States Patent
Kariyone et al.

[11] Patent Number: 5,992,221
[45] Date of Patent: Nov. 30, 1999

[54] CONCENTRATION MEASURING APPARATUS

[75] Inventors: Akio Kariyone; Yoshio Hashizume; Ryuzo Hayashi, all of Hyogo, Japan

[73] Assignee: New Oji Paper Co., Ltd., Tokyo, Japan

[21] Appl. No.: 08/703,700

[22] Filed: Aug. 27, 1996

[30] Foreign Application Priority Data

Aug. 31, 1995 [JP] Japan .................................. 7-248752
Sep. 30, 1995 [JP] Japan .................................. 7-276628

[51] Int. Cl.$^6$ .............................. G01N 1/00; G01N 1/16; G01N 15/06
[52] U.S. Cl. .................... 73/61.59; 73/863.31; 422/68.1
[58] Field of Search ............................. 73/61.59, 61.72, 73/64.56, 863.31, 863.33; 422/68.1, 178

[56] References Cited

U.S. PATENT DOCUMENTS

| | | | |
|---|---|---|---|
| 3,369,405 | 2/1968 | Galegar ........................... | 73/863.21 |
| 3,690,833 | 9/1972 | Ferrari ............................ | 73/61.59 |
| 3,846,075 | 11/1974 | Cioffi ............................. | 73/863.33 |
| 3,878,727 | 4/1975 | Burns . | |
| 4,328,185 | 5/1982 | Reasons et al. .................. | 422/82 |
| 4,525,278 | 6/1985 | Frost ............................... | 210/638 |
| 4,738,781 | 4/1988 | Word et al. ..................... | 210/637 |
| 4,819,478 | 4/1989 | Melcher .......................... | 73/61.1 |
| 4,863,691 | 9/1989 | Noguchi et al. . | |
| 4,993,271 | 2/1991 | Vargason ......................... | 73/61.71 |
| 5,013,436 | 5/1991 | Lee et al. ........................ | 210/321.8 |
| 5,094,817 | 3/1992 | Aoki et al. ...................... | 422/68.1 |
| 5,221,477 | 6/1993 | Melcher et al. ................. | 210/634 |
| 5,368,725 | 11/1994 | Bredewweg et al. ............ | 210/138 |
| 5,492,838 | 2/1996 | Pawliszyn ....................... | 436/178 |
| 5,683,916 | 11/1997 | Goffe et al. ..................... | 436/535 |

FOREIGN PATENT DOCUMENTS

| | | |
|---|---|---|
| 326 995 A2 | 8/1989 | European Pat. Off. . |
| 412 046 A2 | 2/1991 | European Pat. Off. . |
| 467 307 A2 | 1/1992 | European Pat. Off. . |

*Primary Examiner*—Michael Brock
*Assistant Examiner*—Jay L. Politzer
*Attorney, Agent, or Firm*—Nikaido, Marmelstein, Murray & Oram LLP

[57] ABSTRACT

Pipes provided with each switching valve in intermediate portions thereof for feeding sample solutions to a separation mechanism are joined by a multi-way joint, to reach the separation mechanism through a pump. When all valves are closed while driving the pump and thereafter one valve is opened, all bubbles etc. downstream the opened valve are swept and eliminated due to abrupt flow of a liquid since a portion downstream the valve has been decompressed. In switching of a sample in sample measurement, a valve of a pipe for a completely measured sample is left open while a valve of a pipe for a next sample is opened, and then the valve of the pipe for the previously completely measured sample is closed after a while. Thus, pressure fluctuation following sample switching is avoided.

6 Claims, 6 Drawing Sheets

Fig. 6

CONCENTRATION MEASURING APPARATUS

BACKGROUND OF THE INVENTION

1. Field of the Invention

The present invention relates to a measuring apparatus for measuring the concentration of a specific component of a liquid sample, particularly a turbid liquid sample.

2. Description of the Background Art

In a concentration measuring apparatus for a liquid sample, a pipeline comprising a valve having both of a channel connection switching function and a function of sealing an unnecessary piping channel is employed in case of separately guiding a plurality of reagents for measurement such as a moving phase of a buffer solution or the like, a standard solution and a washing solution from respective reservoirs to a reactor, a detector and the like. Such a valve is represented by a multi-way connecting valve.

Th e multi-way connecting valve can prevent contamination resulting from mixing of solutions at a terminal area, thereby attaining accurate measurement. When the sample is prepared from an extremely contaminative one such as a fermentation solution, for example, the detector is disadvantageously contaminated and reduced in accuracy.

When the sample solution is prepared from a fermentation solution or the like, the sample solution is kept seperate from a liquid flowing through a detecting mechanism until these solutions are brought into contact with each other through a film such as an ultrafiltration membrane, a dialysis membrane or a filter employed to prevent the detecting part from being contaminated with micro-organisms or the like. When the solutions are brought into contact with each other through the film, part of the sample solution or chemical substances dissolved therein is transferred into the liquid flowing in the detecting mechanism through the film.

The micro-organisms or a contamination source can be eliminated from the detecting part side by detecting the transferred sample solution or chemical substances.

Also when such a separation device having a film is employed, however, the sample solution generally contains a large quantity of gas such as carbon dioxide following proliferation of micro-organisms, in the case of a fermentation solution or the like. When such gas forms bubbles in the pipeline, the flow of the liquid is disturbed to readily cause reduction of accuracy.

In an apparatus having a separation mechanism through a film, further, pressure fluctuation may be transmitted to the film to cause reduction of accuracy when a plurality of sample solutions are switched.

When a sample is used, which contains a solid which tends to prevent a valve from sealing, not only sealing by the valve but switching of channels is made incomplete since the multi-way connecting valve performs switching of connection of the channels and sealing of unnecessary pipes by sliding of a valve element, and hence mutual contamination is disadvantageously readily caused by mixing of the solutions at the connecting part.

In order to open/close a pipe passing a solution containing a solid or the like therethrough, on the other hand, a valve, such as a pinch valve, for example, which presses and seals a pipe having elasticity over a length of several mm to several cm, for example, exceeding the inner diameter of the pipe is effective. Even if a solid of a size exceeding the inner diameter of the pipe enters the pipe, the valve presses and seals the pipe in a range beyond the size of the solid while the pressed elastic pipe is changed to the shape of the solid. Thus, the valve has high sealability for a sample containing a solid, although the same has no channel switching function. However, mixing of solutions at the pipe connecting part is unavoidable since the connecting part has no function of sealing unnecessary pipe channels. Thus, occurrence of mutual contamination and reduction of measuring accuracy are unavoidable.

When three pipelines for a standard solution, a sample solution and a washing solution, for example, are unified and guided to a pipeline reaching a measuring part with respect to such problems, there is a method of employing a four-way joint and connecting the three pipelines in one portion. In this method, the standard solution of a known concentration value and washing water are mixed into the sample solution in a certain ratio when the sample solution is passed, while it is conceivable that there is no problem if correction is performed. When the standard solution is passed, however, the sample solution of unknown concentration is mixed and hence no correct measurement result is obtained. Since the sample solution and the standard solution come into contact with each other, further, micro-organisms propagate in the connecting part through a nutrition source of a component of the standard solution such as glucose, for example, in case of a sample such as a fermentation solution containing micro-organisms, to unpreferably readily cause a problem such as clogging of the pipe by proliferated fungus bodies.

As a method of avoiding propagation of micro-organisms or the like, it is effective to construct a pipeline with employment of a three-way joint, so that the sample solution and the standard solution are not in direct contact with each other. Due to employment of the three-way joint, however, the state of contamination by mixing of the solutions is disadvantageously further complicated. When two or more pipelines are provided, pipe connecting parts are present in a plurality of portions due to employment of the three-way joint. Solution contamination is not necessarily caused at the same degrees in respective pipe connecting parts, leading to lack in reproducibility of measurement.

For example, there is a method of connecting reference and sample solution pipelines each comprising a pinch valve with each other by a three-way joint for joining the same with each other, and connecting the joined pipelines with a washing solution pipeline by another three-way joint, for guiding the same to a pump. In this piping state, however, the standard solution of constant concentration is regularly in contact with the sample solution having indeterminate concentration on an upstream connecting part, and no correct measurement result is obtained. This is because the concentration of the standard solution is instable since the concentration of a target substance in the sample solution is indeterminate, even if the degree of mutual contamination of the reference and sample solutions has reproducibility in view of only the rate of solution volumes. In these pipelines, further, the reference and sample solutions come into contact with each other, leading to a problem such as propagation of micro-organisms similarly to the case of employing a four-way joint.

There is another method of connecting sample and washing solution pipelines each comprising a pinch valve with each other by a three-way joint for joining the same, and connecting a standard solution pipeline comprising still another pinch valve to the joined pipelines by another three-way joint. In this case, the sample solution having indeterminate concentration or the washing solution which is contaminated with the sample solution having indeterminate concentration is regularly in contact with the standard solution. Further, positional difference is inevitably caused between the sample solution pipeline connecting part and the standard solution pipeline connecting part with respect to a pump, and difference is readily caused in degrees of transmission of suction force from the pump. Consequently, difference is readily caused between degrees of mutual contamination of the sample and washing solutions in a position separated from the pump and that in a position close to the pump. Thus, no reproducibility of measurement is attained but only an incorrect result of measurement is obtained in this case.

There is still another method of connecting reference and washing solution pipelines each comprising a pinch valve with each other by a three-way joint for joining the same, and connecting a sample solution pipeline comprising still another pinch valve to the joined pipelines by another three-way joint. In this case, the standard solution or the washing solution which is contaminated with the standard solution is regularly in contact with the sample solution while positional difference is inevitably caused between the sample solution pipeline connecting part and the standard solution pipeline connecting part with respect to a pump, and no reproducibility of measurement is attained but only an incorrect result of measurement is obtained also in this case.

Thus, it is difficult to form a channel while eliminating problems with respect to a sample containing solids, avoiding direct contact between sample and standard solutions, and attaining reproducibility of measurement.

SUMMARY OF THE INVENTION

A first object of the present invention is to prevent a pipe from collection of bubbles which are formed by gas.

A second object of the present invention is to prevent pressure fluctuation from being transmitted to a film and reducing accuracy in case of switching a plurality of sample solutions in an apparatus having a separation mechanism through the film.

A third object of the present invention is to enable application to a sample containing a solid, avoid direct contact between sample and standard solutions, and attain reproducibility of measurement.

The present invention provides a concentration measuring apparatus comprising a separation mechanism having a porous film and channels allowing flow of liquids in contact with both surfaces of the film for transferring a target substance between the liquids of the channels through the film, a first liquid feed channel which can make a solution containing the target substance flow in one of the channels on the first surface of the film of the separation mechanism, a second liquid feed channel making a liquid containing no target substance flow in the other channel on the second surface of the film of the separation mechanism, and a detecting part which is provided downstream the second surface of the film of the separation mechanism for measuring the target substance. The first liquid feed channel comprises a pipe group at least comprising a plurality of pipes guiding a plurality of solutions containing the target substance respectively, switching mechanisms which are provided in intermediate portions of the respective pipes of the pipe group and capable of switching the channel at arbitrary points of time, a joining mechanism which is provided downstream the switching mechanisms for joining the pipes with each other, and a liquid feed mechanism which is provided downstream the joining mechanism for sucking and discharging liquids, while the concentration measuring apparatus further comprises a control unit controlling switching operations of the switching mechanisms and ON/OFF operations of the liquid feed mechanism.

The porous film used in the separation mechanism is a film possessing a separate function.

The control unit preferably comprises switching mechanism control means which makes control for closing all switching mechanisms in advance of measurement, starting suction and discharge of the liquid feed mechanism for bringing the pipes into decompressed states, and thereafter opening a switching mechanism for a pipe of at least one sample solution. Due to this structure, it is possible to prevent bubbles from remaining in the pipes, thereby preventing reduction of accuracy. High-accuracy measurement is enabled in a simple method also as to a sample such as a fermentation solution, for example, which contains admixtures and bacteria, readily blocks conduits and contaminates a detector, and generates bubbles.

Further, it is possible to prevent liquids from flowing back from the pipes to a sample solution tank such as a fermentation tank, for example, which is connected to the pipe for the sample solutions, by making control for opening the switching mechanisms for the pipes of the sample solutions after bringing the pipes into decompressed states. Thus, it is possible to prevent the fermentation tank or the like from being contaminated.

It is also preferable that the control unit comprises switching mechanism control means making control for superposing times holding open states of a switching mechanism for a pipe of one sample solution which is completely measured and a switching mechanism for a pipe of another sample solution at the time of switching one sample solution to another sample solution in measurement and thereafter closing the switching mechanism for the pipe of the one sample solution. Due to this structure, it is possible to prevent pressure fluctuation in switching from being transmitted to the film of the separation mechanism, and measurement accuracy is improved also in this viewpoint.

According to another preferred embodiment, the first liquid feed channel includes a plurality of pipes feeding solutions containing the target substance and a pipe feeding a liquid containing no target substance, and the joining mechanism includes a first multi-way joint dividing the pipe feeding the liquid containing no target substance into channels of the same number as conduits feeding liquids containing the target substance, a three-way joint group set-connecting respective ones of the channels which are formed by dividing a channel feeding the liquid containing no target substance by the first multi-way joint with respective ones of the pipes feeding liquids containing the target substance in one-to-one relation, and a second multi-way joint set-connecting the respective channels which are set-connected by the three-way joint group by pipes of the same length and the same internal diameter for finally connecting the same into a single pipe. Due to this structure, valves simply opening/closing the respective channels are employed for connecting the channels in a fork manner in case of switching the sample solution, a reference sample solution and a washing solution and allowing flow thereof for feeding the same to the separation mechanism, whereby the valves can be prepared from arbitrary switching valves. For example, pinch valves can be employed also when the sample solution contains solids, whereby implementation can be attained in a simple and low-priced structure. Even if dead spaces are formed in the channels following switching thereof, the sample solution comes into contact with only a liquid containing no target substance, whereby high accuracy can be attained.

In still another preferred embodiment, the first multi-way joint for the pipe for the liquid containing no target substance first dividing the channel in plural in a portion downstream the switching mechanisms with respect to a direction for feeding the liquid is provided at lower position than the second multi-way joint finally connecting the set-connected channels into a single pipe with respect to a horizontal plane. Due to this structure, bubbles which are present in the pipes are quickly passed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS (Embodiment 1)

Figure 1:
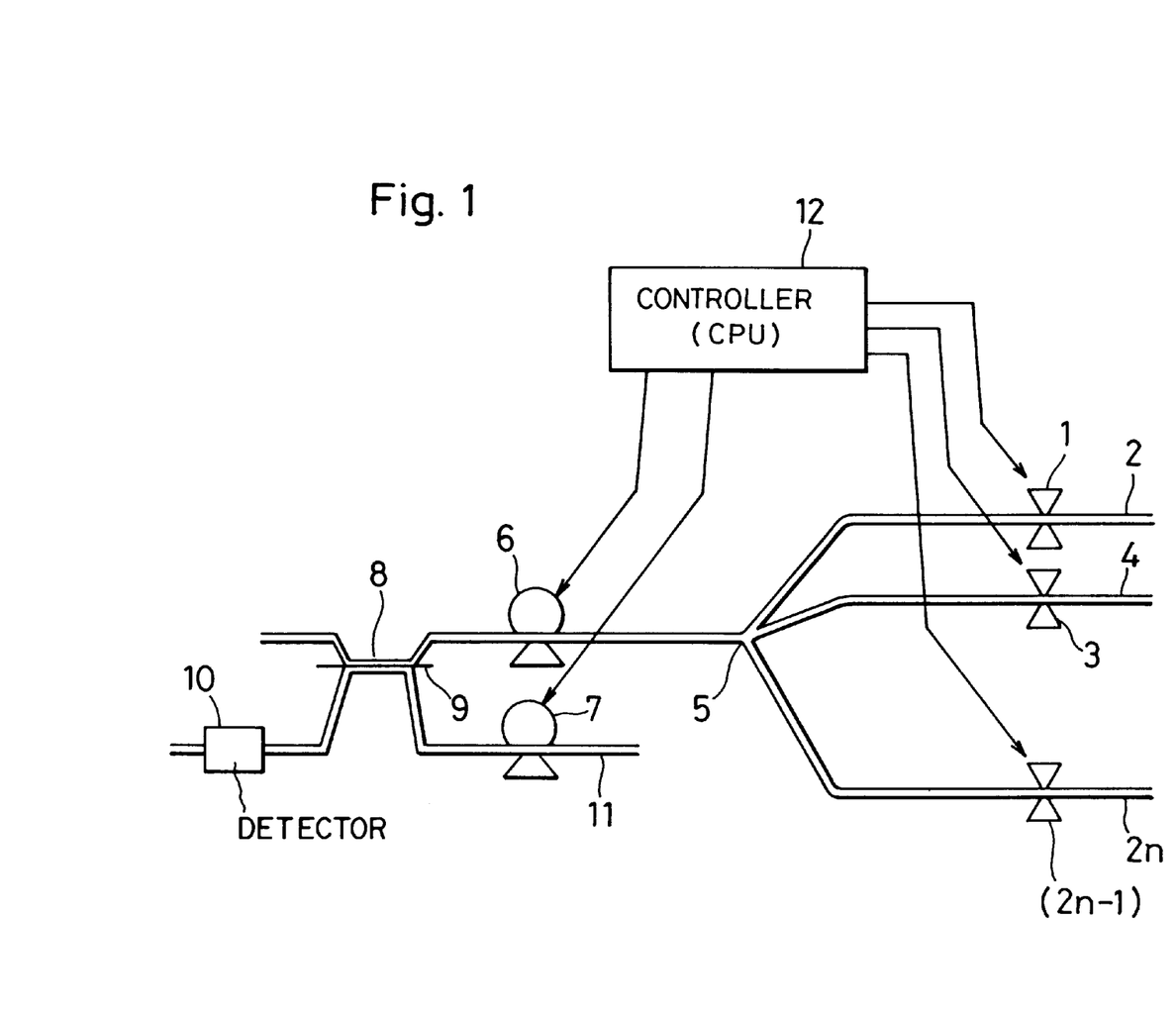
FIG. 1 is a schematic block diagram showing a first embodiment of the present invention.

A first embodiment of the present invention is described with reference to FIG. 1. Numerals 2, 4, . . . , 2n denote pipes for feeding sample solutions to a measuring part, and switching valves 1, 3, . . . , 2n+1 are inserted in intermediate portions thereof respectively. The pipes 2, 4, . . . are joined with each other by a multi-way joint 5, to reach a separation mechanism 8 through a pump 6. The separation mechanism 8 is divided into two spaces by a separation film 9, so that the sample solutions which are fed from the pipes 2, 4, . . . are discharged through the space above the separation film 9 in FIG. 1. A liquid containing no sample component, such as a buffer solution, for example, is fed to the space under the film 9 of the separation mechanism 8 in FIG. 1 through a pipe 11 by a pump 7. Sample components which are transferred from the sample solutions in the upper space into the liquid in the lower space through the film 9 are fed to a detector 10. Numeral 12 denotes a control unit which controls switching operations of the valves 1, 3, . . . , 2n+1 and ON/OFF operations of the pumps 6 and 7.

When all valves 1, 3, . . . are closed while driving the pump 6 and thereafter one valve is opened in the aforementioned structure, all bubbles etc. downstream the open valve are swept and eliminated due to abrupt flow of the liquid since portions downstream the valves 1, 3, . . . have been decompressed. When such operations are successively performed as to the valves 1, 3, . . . , bubbles are eliminated from all pipes 2, 4, . . . .

While it is possible to simultaneously open two or more valves, it is predicted that bubbles remain in this case, and hence only one valve is preferably opened. While the operation for opening/closing the valve for eliminating bubbles is preferably performed once as to every one of the valves 1, 3, . . . , the same may be omitted depending on conditions. For example, the bubble eliminating operation can be omitted as to valves and pipes for sample solutions hardly generating bubbles, or the operation may be performed only on valves and pipes for sample solutions which must be quickly measured.

Thereafter sample measurement is performed. In case of sample switching, the valve for the pipe of a sample which is currently measured is left open while that for the pipe of a next sample is opened, and the valve for the pipe of the previously measured sample is closed after a while. Thus, pressure fluctuation following sample switching is avoided.

According to the present invention, materials and thicknesses of tubes forming pipelines are not particularly restricted. When pinch valves are employed, however, at least portions of the pipelines held by the pinch valves are preferably formed by elastic members having restoring force such as silicone tubes, vinyl chloride resin tubes or polyolefin tubes, for example. In particular, polyolefin tubes are preferable since polyolefin have such low gas permeability that air hardly penetrates from tube outer walls during stoppage of liquids and bubbles are hardly generated. Tubes which are made of a fluororesin material or a rubber material are also preferable.

A two- to four-way joint is employed for joining these tubes with each other. The structure of the joint is not particularly restricted either, while a joint of a material such as a metal or hard plastic which is harder than the tubes is preferable since a method of mounting the tubes is simplified. The joint is preferably made of fluororesin, polypropylene or polyethylene, since the materials are easy to work and can be prepared in various modes, and corrosion is hardly caused by the liquid flowing therein dissimilarly to a metal. Further, a joint of fluororesin or polypropylene is preferable for feeding a fermentation liquid since the materials are capable of pressurized steam sterilization.

While the valves are prepared from various types of valves such as pinch valves, electromagnetic valves and motor-driven multi-way valves, it is necessary to select internal pipe diameters, in order to prevent clogging by turbidness of the sample solutions. The pinch valves are most advantageous in view of clogging, since the employed pipes are employed for closing channels as such.

In more concrete terms, basic pipelines of the concentration measuring apparatus according to the present invention are as follows:

A plurality of pipelines each comprising a pinch valve are prepared, and parts of pipes are held by the pinch valves. A joint for joining is provided downstream the portions provided with the pinch valves with respect to the directions of flow of liquids, so that the sample solutions are guided to a pump for sucking and discharging samples through the joint, and guided into a channel provided on one side of a film of a separation mechanism comprising the film through the pump. The pump may be provided either in front or at the back of the separation mechanism. In general, the pump is preferably provided in front of the separation mechanism for sample introduction by pressure when the channel in the separation mechanism is so thin that there is a possibility that a back pressure in passage is increased. While the pump may be selected from various ones such as a gear pump, a plunger pump and a tube pump. Since the tube pump stroking a tube for feeding liquids is low-priced, the tube pump is preferable for a purpose of feeding sample solutions having turbidity. The tube employed for the tube pump can be selected from various ones similarly to those employed for the pipes, while a polyolefin tube which can attain long-term liquid feed rate stability is preferable.

An ultrafiltration membrane, a dialysis membrane or a membrane filter can be illustrated as the film which is employed in the separation mechanism having the film. A polysulfone film, a cellulose acetate film or the like can be illustrated as the ultrafiltration membrane, while various film materials can be utilized depending on the target substances to be separated and measured. A regenerated cellulose film or the like is employed as the dialysis membrane. The membrane filter is made of fluororesin, polycarbonate, regenerated cellulose or nitrocellulose. When water-soluble low molecules are to be measured, the strong dialysis membrane having low necessity for pressurization is preferably employed. In order to gasify and transfer ammonia or alcohol which is dissolved in water, a fluororesin membrane filter having a filter pore size of about 0.1 to 1.0 $\mu$m is so utilized as to form a kind of gas permeation film transferring only a target substance, whereby it is possible to further effectively prevent unnecessary components from reaching a detector.

In order to detect the target substances, a known detector such as an absorption photometer, a fluorophotometer, a pH meter, an ion electrode, a semiconductor ion sensor, an electrochemical detector, an atomic absorption photometer, an induced plasma emission spectrophotometer, an enzyme electrode, a heat measurer or the like is employed. It is also possible to cause chemical reaction in the channel for detecting physical quantities changed as the result, or to introduce a fermentation solution into a separation column after eliminating fungus bodies or the like therefrom, to connect the same with the so-called liquid chromatograph.

In case of analyzing a remarkably contaminated sample such as a fermentation solution, pipes guiding a plurality of sample solutions to the separation mechanism are opened/closed by pinch valves, while all these pipes are closed and pump such as tube pump is driven so that the pipes enter decompressed states. Thereafter a certain pinch valve is opened, whereby a liquid abruptly flows into the decompressed pipes so that bubbles are swept and eliminated. If necessary, this operation may be performed on a specific sample solution pipeline so that thereafter all pinch valves are closed for re-decompression and bubbles of another pipeline are eliminated. As to the time for entirely closing the pinch valves for such decompression, 1 to 10 seconds are empirically effective in case of feeding at about 1 ml/min. in pipelines of about 2 mm in inner diameter, depending on the flow rates of tube pumps employed for feeding and the types of the solutions. Pressure balance in the pipes is damaged for about 1 to 20 seconds after the bubble eliminating operation, and hence the transfer rates of the target substances in the pipes are also ready to fluctuate. Thus, it is preferable not to employ concentration measurement values of the detector during this period. Elimination of bubbles by decompression is effective also when the viscosity levels of the sample solutions are so high that bubbles are hardly eliminated, and it is possible to eliminate bubbles contained in samples having viscosity levels of not more than 3000 cp. The viscosity of an ordinary fermentation solution is 10 to 2000 cp, and this method is applicable to a number of fermentation solutions.

Then, channels are successively switched to perform measurement after completion of the bubble eliminating operation. When the operation is switched to a second sample solution after starting of suction and discharge of a first sample solution, damage of pressure balance in the pipes can be prevented by temporarily opening both pinch valves which are provided for respective pipelines feeding the first and second sample solutions and thereafter closing the pinch valve for the first sample solution. Concentration detection can be continuously performed due to this treatment, whereby efficiency of measurement can be improved. At least one of the sample solutions may be a standard solution for calibrating the apparatus.

Due to such a mechanism and operation procedure, it is possible to prevent bubbles from remaining in the pipes, prevent reduction of accuracy, and prevent pressure fluctuation in switching from being transmitted to the film, thereby enabling increase in accuracy and improvement in efficiency.

While exemplary analysis of a fermentation solution in alcohol fermentation by yeast is shown as a concrete embodiment 2, the present invention is not restricted to such a concrete example.

(Embodiment 2)

Figure 2:
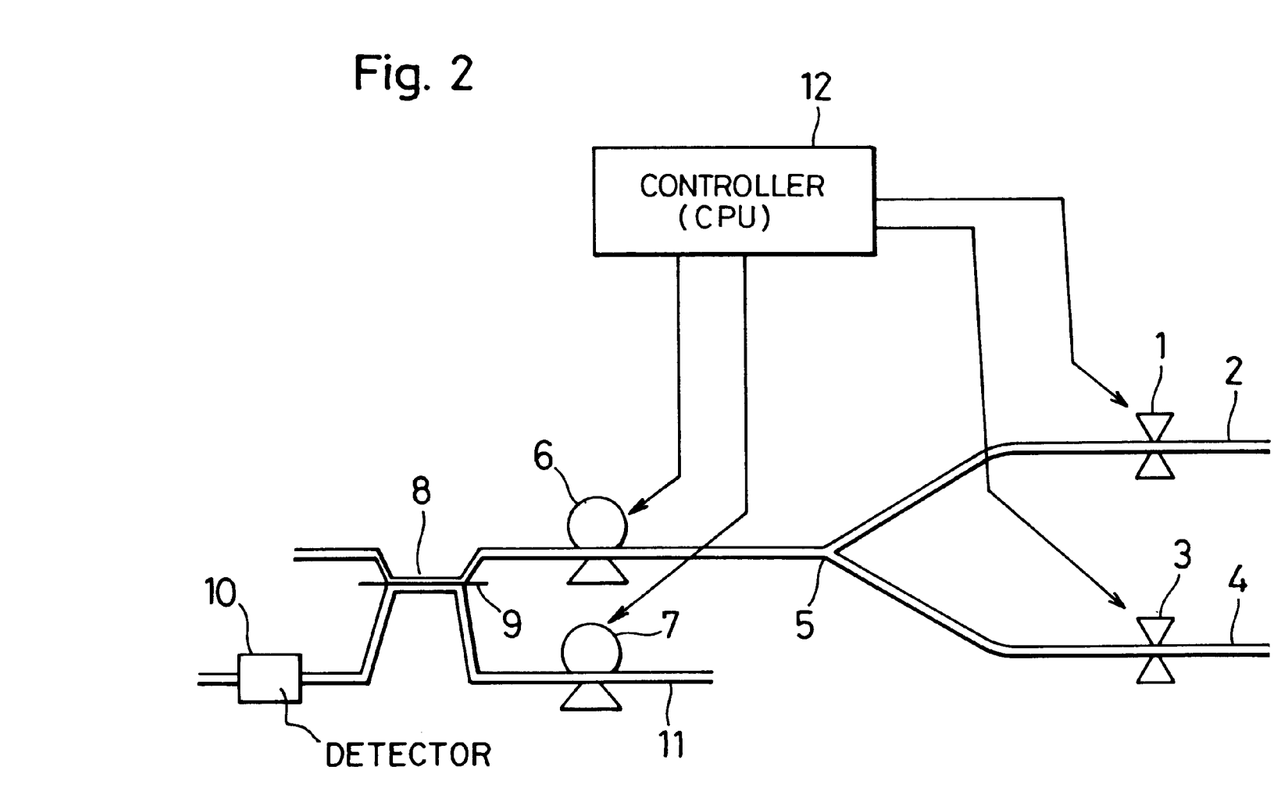
FIG. 2 is a schematic block diagram showing a second embodiment of the present invention.

As shown in FIG. 2, a first sample solution pipe 2 which is formed by a silicone tube of 4 mm in outer diameter and 2 mm in inner diameter and a pinch valve 1 and a second sample solution pipe 4 which is similarly formed are connected by a three-way joint 5 of polypropylene to be joined with each other. The joined pipe is guided to a space on one side of a separation mechanism 8 through a first liquid feed tube pump 6. The tube pump 6 can suck and feed a liquid at a flow rate of 2 ml/min.

A regenerated cellulose dialysis membrane 9 of 20 $\mu$m in thickness is mounted on the separation mechanism 8, while a 0.1 M phosphoric acid buffer solution of pH 7.0 is fed in a space on the opposite side (lower side in FIG. 2) of the film 9 by a second liquid feed tube pump 7. A detector 10, provided with an enzyme electrode to which glucose oxidase is fixed, is provided downstream the space on the lower side of the separation film 9 in the separation mechanism 8, to measure glucose concentration values of fermentation solutions flowing thereinto from the sample solution pipes 2 and 4.

Pinch valves 1 and 3 are inserted in intermediate portions of the pipes 2 and 4. The fermentation solutions flowing through the pipes 2 and 4 had absorbance values of 12.0 and 1.0 at 660 nm and temperatures of 15° C. and 10° C. respectively. When the room temperature was 25° C., large quantities of bubbles were recognized in the pipes 2 and 4 which were filled with the fermentation solutions.

Figure 3:
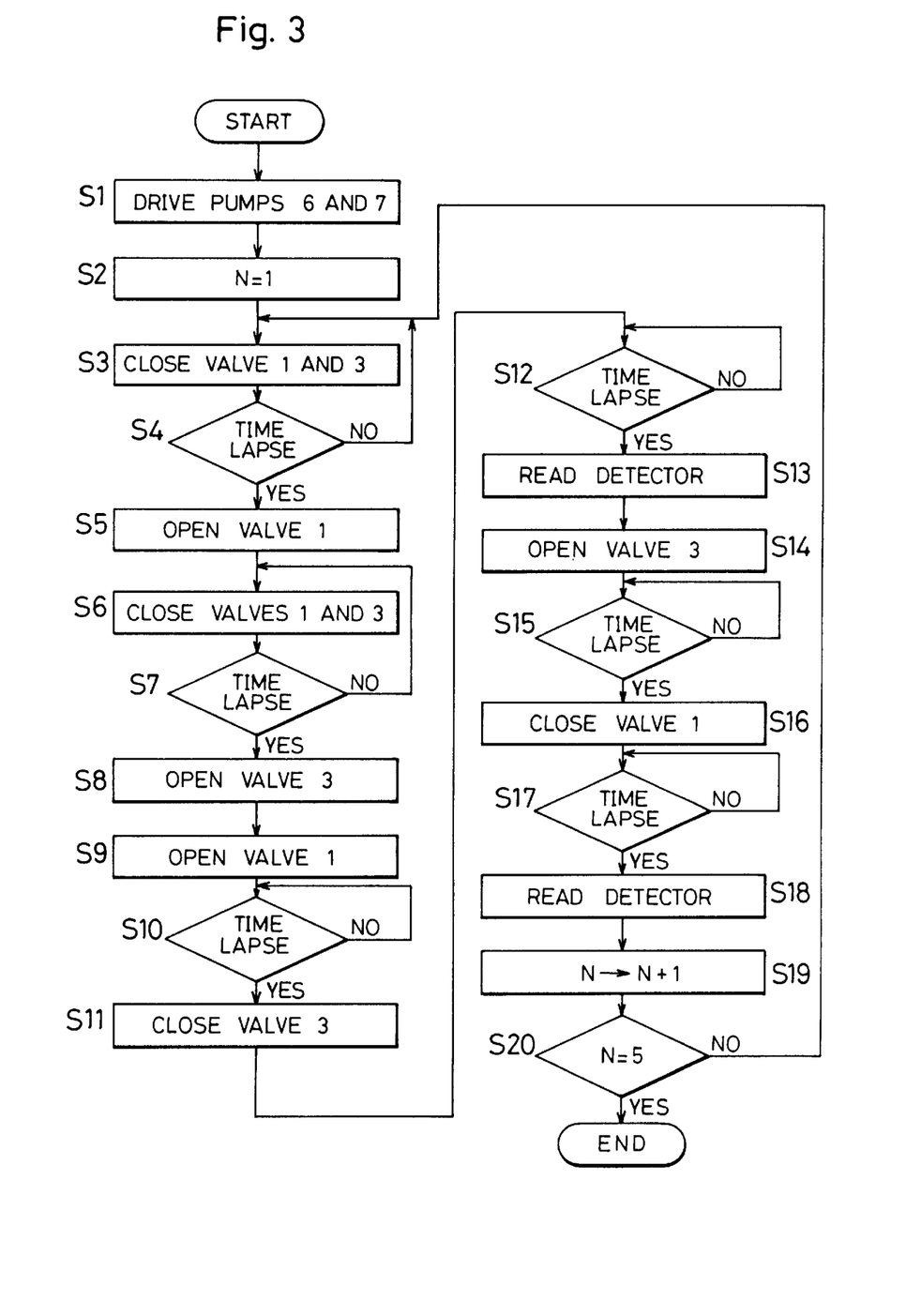
FIG. 3 is a flow chart showing operations in the embodiment shown in FIG. 2.

A standard glucose solution was previously fed in the pipe 2 for calibrating the enzyme electrode 10, and thereafter an operation was made by a control unit 12 as shown in a flow chart of FIG. 3. The tube pumps 6 and 7 were driven (S1), and a decompression operation was performed for 10 seconds in a state closing the pinch valves 1 and 3 (S2, S3 and S4). Thereafter the pinch valve 1 was opened to guide the fermentation solution to the separation mechanism 8, whereby bubbles were eliminated from the pipe 2 (S5). Then, a decompression operation was performed again for 10 seconds in the state closing the pinch valves 1 and 3 while keeping the tube pumps 6 and 7 driven (S6 and S7), and thereafter the pinch valve 3 was opened (S8), whereby bubbles were eliminated also from the pipe 4.

Then, the pinch valve 1 was also opened in the open state of the pinch valve 3 (S9), and only the pinch valve 3 was closed after a lapse of 1 second (S10 and S11). Since the tube pumps 6 and 7 were continuously rotated, the output value of the enzyme electrode 10 was gradually increased to be constant after 120 seconds (S12). The current value was read (S13) for calculating glucose concentration in the fermentation solution guided by the pipe 2, which was 0.15%.

Then, the pinch valve 3 was also opened in the open state of the pinch valve 1 (S14), and only the pinch valve 1 was closed after a lapse of 1 second (S15 and S16). Glucose concentration in the fermentation solution guided by the pipe 4 which was calculated from the current measured value was 1.0% (S17 and S18).

Thereafter the pinch valves were switched in the aforementioned system to repeatedly measure the respective samples five times (S19 and S20) for obtaining fluctuation coefficients of measured values, which were ±3.0% and ±2.5% respectively.

COMPARATIVE EXAMPLE 1

In the apparatus shown in FIG. 2, measurement was repeatedly made similarly to the embodiment 2, without closing both of the pinch valves 1 and 3, i.e., without producing decompressed states. In this case, bubbles remained in the separation mechanism 8, and accuracy was ±5% in relation to that of the pipe 2 and ±6.5% with respect to that of the pipe 4.

COMPARATIVE EXAMPLE 2

Both of the pinch valves 1 and 3 were closed to produce decompressed states and eliminate bubbles, and a measuring operation identical to that of the embodiment 2 was repeated. When pinch valve opening was switched from the pipe 2 to the pipe 4, a method of not opening both pinch valves 1 and 3 but closing either one was employed.

Consequently, accuracy in relation to the fermentation solution of the pipe 2 was ±7.0%, and that related to the pipe 4 was ±6.0%.

(Embodiment 3)

Figure 4:
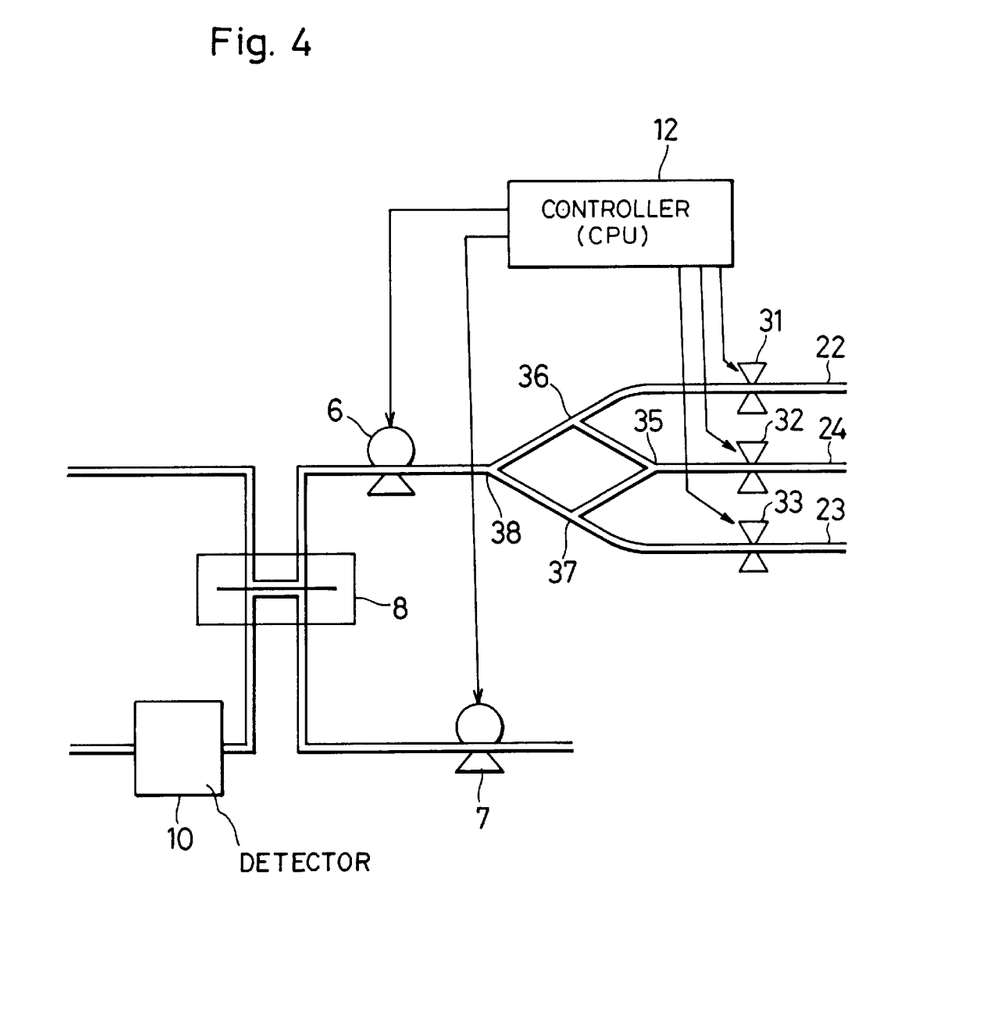
FIG. 4 is a schematic block diagram showing a third embodiment of the present invention.

An embodiment further comprising a pipe structure avoiding direct contact between sample and standard solutions is described with reference to FIG. 4.

Three systems of pipelines comprising pinch valves 31, 32 and 33 respectively are formed so that two systems 22 and 23 are pipelines for liquids which may contain target substances while the remaining system 24 is employed as a pipeline for a liquid containing no target substance.

The pipeline 24 containing no target substance is divided into two channels through a three-way joint 35 serving as a first multi-way joint which is arranged downstream the pinch valve 32 providing portion with respect to the direction of flow of the liquid.

One of the channels for the liquid containing no target substance is connected with the pipeline 22, comprising the pinch valve 31, for a first liquid which may contain a target substance, by a first three-way joint 36. The other one of the channels for the liquid containing no target substance is connected with the pipeline 23, comprising the pinch valve 33, for a second liquid which may contain a target substance, by a second three-way joint 37.

The pipelines from the first and second three-way joints 36 and 37 are connected by a three-way joint 38 serving as a second multi-way joint and joined with each other, and the joined pipe is guided to a space on one side of a separation mechanism 8.

At this time, pipes connecting the first and second three-way joints 36, 37 with the second multi-way joint 38 respectively may not necessarily be identical in inner diameter and pipe length to each other. When liquid feed means such as a liquid feed pump is provided upstream, however, the pipes preferably have the same inner diameters and pipe lengths, in order to regularize influences exerted by the liquid feed pump on solution mixing in pipe connection parts at about the same degrees.

When such pipelines are structured, there is such an advantage that only a single pinch valve 32 can be provided in the pipeline feeding the liquid containing no target substance and the apparatus structure is simplified as compared with a case of independently providing a pipeline feeding a liquid containing no target substance connected with the pipeline 22 feeding a first liquid which may contain a target substance and a pipeline feeding a liquid containing no target substance connected with the pipeline 23 feeding a second liquid which may contain a target substance.

Assuming that the first and second liquids which may contain target substances are a sample solution and a standard solution respectively, that which comes into direct contact with the sample and standard solutions can be the liquid containing no target substance, such as a washing solution, for example, whereby there occurs no such phenomenon that micro-organisms contained in the sample propagate through a nutrition source of substances contained in the standard solution to block the pipes.

Also when a liquid feed mechanism 6 such as a stroking pump is provided on an intermediate portion of a pipe reaching the separation mechanism from the second multi-way joint 38, the first and second three-way joints 36 and 37 connected with the pipes 22 and 23 feeding the first and second liquids which may contain target substances can be arranged in equivalent positional relation from the liquid feed mechanism 6, whereby numbers of pipe connecting parts by three-way joints passed before reaching the separation mechanism 8 can be equalized. Namely, it is possible to cancel an influence exerted by a solution containing no target substance on solutions which may contain target substances by equalizing conditions exerted on mutual mixing with the solution containing no target substance.

Assuming that a standard solution is diluted to concentration of X times due to contamination with a washing solution upon passage of the standard solution, for example, the degree of an influence thereof is equivalent also in case of passing a sample solution, and it comes to that concentration A of a target substance in the sample solution is diluted to A×X. When the sample solution which is diluted to A×X by the standard solution diluted to X times is measured, therefore, influences exerted by dilution caused by mixing of the washing solution cancel with each other, whereby correct concentration A can be measured.

The pipelines thus formed can be introduced into the separation mechanism 8 since the pipelines are integrated into a single system pipeline by the second multi-way joint 38.

Branched/integrated arboroid pipes consisting of the two pipes 22 and 23 for the solutions which may contain target substances and the single pipe 24 for the solution containing no target substance are further employed in plural and finally integrated into a single system pipeline, to be connected to the pipeline finally reaching the separation mechanism 8. Also in this case, pipelines for solutions containing no target substances can be branched into the same numbers of channels as those of the pipelines feeding the solutions which may contain target substances through a plurality of three-way joints to be independently connected with each other through the three-way joints, thereby reducing the number of pinch valves provided for the pipelines for the solutions containing no target substances.

When the multi-way joint 35 first dividing the pipe for the liquid containing no target substance into two channels in a portion downstream a switching mechanism with respect to the direction for feeding the liquid is provided at lower position with respect to a horizontal plane than the multi-way joint 38 finally connecting the set-connected pipelines into a single pipeline, it is preferable since bubbles such as those present in the pipelines brought by foaming samples, for example, are quickly passed.

The number of channels for the liquid containing no target substance is not restricted to two, but decided in response to the number of channels for liquids containing target substances. Concrete examples of the channels in the embodiment shown in FIG. 4 are now described.

A glucose standard solution pips 22 formed by a silicone tube of 4 mm in outer diameter and 2 mm in inner diameter and a pinch valve 1, a similarly formed sample solution pipe 23 and a washing solution pipe 24 were connected with each other by a plastic three-way joint 38, and guided to a space on one side of a separation mechanism 8 through a liquid feed peristaltic pump 6. A moving phase was fed to a space on the other side of the separation mechanism 8 by a peristaltic pump 7, so that glucose which was transferred into the moving phase through a film of the separation mechanism 8 was guided to a glucose detector 10 and detected.

The washing solution pipe 24 was connected to a three-way joint 35 which was a first multi-way joint from a washing solution reservoir through a pinch valve 32, and divided into two channels by connecting two silicone tubes of 4 mm in outer diameter, 2 mm in inner diameter and 100 mm in length to the three-way joint 35. The two channels of the washing solution pipe 24 were connected with the standard solution pipe 22 and the sample solution pipe 23 through first and second three-way joints 36 and 37 respectively.

The first and second three-way joints 36 and 37 were connected with a three-way joint 38 which was a second multi-way joint through silicone tubes of 4 mm in outer diameter, 2 mm in inner diameter and 100 mm in length respectively, thereby integrating the pipelines into one system, which in turn was connected to the separation mechanism 8 through the peristaltic pump 6.

The overall pipelines were so arranged that the three-way joint 35 was held at lower position with respect to a horizontal plane than the three-way joint 38.

The glucose detector 10, which was provided with a fixation enzyme electrode to which glucose oxidase was fixed, was capable of obtaining output signals proportionate to glucose concentration values in fed solutions.

The standard solution was prepared from a 3.6% glucose solution, and solutions containing glucose in respective concentration values were fed as samples for performing measurement.

The standard solution was fed to the separation mechanism 8 by the peristaltic pump 6 in a state of opening a pinch valve 31 provided on the standard solution pipe 22 and closing a pinch valve 33 provided on the sample solution pipe 23, and an output signal of glucose transferred into a moving phase in the separation mechanism 8 and detected by the glucose detector 10 was recorded.

Then, the pinch valve 31 provided on the standard solution pipe 22 was closed, the pinch valve 32 provided on the washing solution pipe 24 was opened, and washing water was fed to the separation mechanism 8 by the peristaltic pump 6.

Thereafter the pinch valve 32 provided on the washing solution pipe 24 was closed, the pinch valve 33 provided on the sample solution pipe 23 was opened, a liquid was fed to the separation mechanism 8 by the peristaltic pump 6, and an output signal of glucose transferred into a moving phase in the separation mechanism 8 and detected by the glucose detector 10 was recorded.

Then, the pinch valve 33 provided on the sample solution pipe 23 was closed, the pinch valve 32 provided on the washing solution pipe 24 was opened, and washing water was fed to the separation mechanism 8 by the peristaltic pump 6.

A glucose detected value in the sample solution was obtained from the ratio of the output signal obtained by feeding the sample solution to that obtained by feeding the standard solution.

Table 1 shows the results.

An intercept of a regressive straight line was small, and inclination was about 1.0. Namely, correct measurement values were obtained.

TABLE 1

| Glucose concentration in sample | Detected value |
|---|---|
| 0.00% | 0.075% |
| 0.45% | 0.53% |
| 0.90% | 0.90% |
| 1.80% | 1.82% |
| 2.70% | 2.78% |
| 3.60% | 3.63% |
| 4.50% | 4.51% |
| Inclination | 0.999 |
| Intercept | 0.03 |
| Coefficient of correlation | 1.000 |

Opening/closing of the pinch valves 31, 32 and 33 may be so switched that there are operations of eliminating bubbles from the pipes 22 and 23 and such a state that two of the pinch valves 31, 32 and 33 are opened for suppressing pressure fluctuation, in accordance with the flow chart of FIG. 3.

COMPARATIVE EXAMPLE 3

Figure 5:
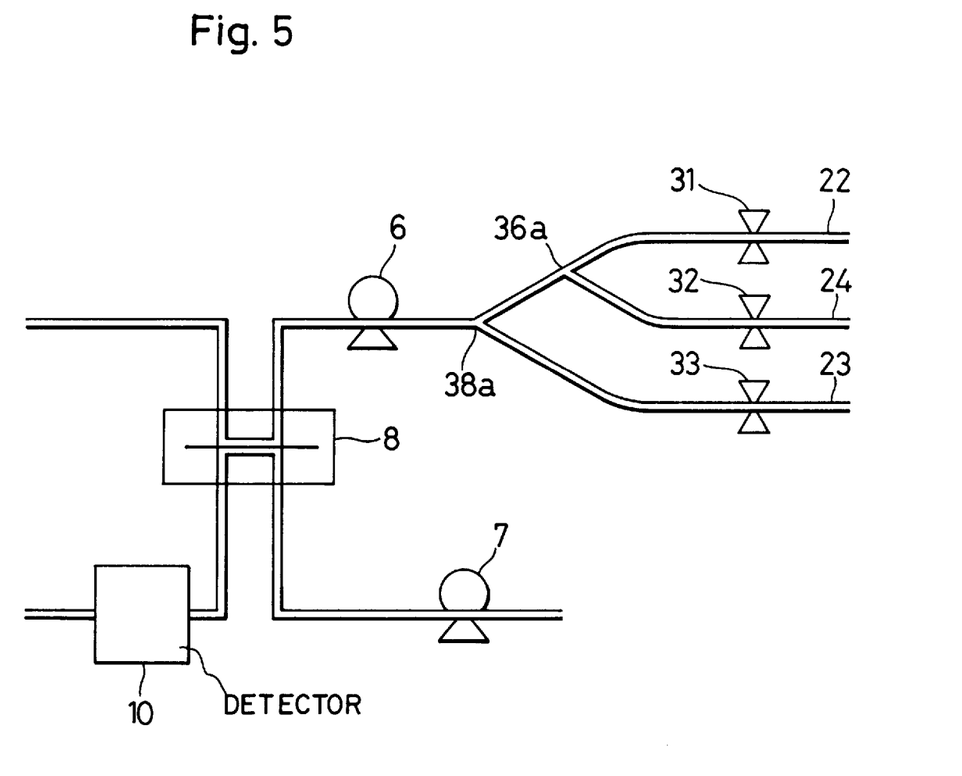
FIG. 5 is a schematic block diagram showing comparative example.

As shown in FIG. 5, a glucose standard solution pipe 32 formed by a silicone tube of 4 mm in outer diameter and 2 mm in inner diameter and a pinch valve 31, a similarly formed sample solution pipe 33 and a washing solution pipe 34 were connected with each other by a three-way joint 38a, and guided to a space on one side of a separation mechanism 8 through a liquid feed peristaltic pump 6 to form a concentration measuring apparatus. As compared with the apparatus shown in FIG. 4, this apparatus is different in a point that the washing solution pipe 24 was connected only with the standard solution pipe 22 through a three-way joint 36a, and not directly connected with the sample solution pipe 33.

Measurement similar to that in the embodiment 3 was performed, to obtain results shown in Table 2. An intercept of a regression straight line was large as compared with that in the embodiment 3, and inclination was smaller than 1. Namely, the measured values were incorrect.

TABLE 2

| Glucose concentration in sample | Detected value |
|---|---|
| 0.50% | 0.60% |
| 1.80% | 1.92% |
| 3.60% | 3.53% |
| Inclination | 0.942 |
| Intercept | 1.92 |
| Coefficient of correlation | 0.999 |

(Embodiment 4)

Figure 6:
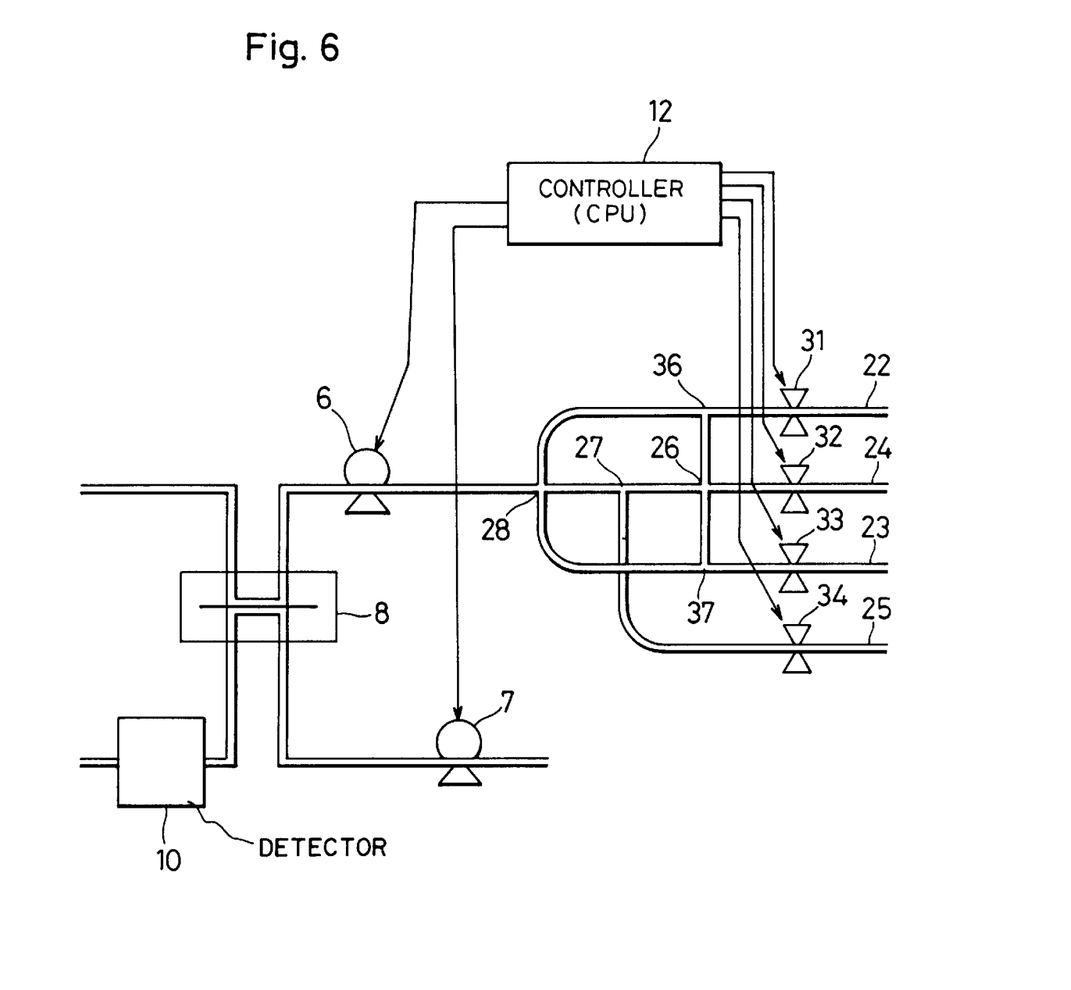
FIG. 6 is a schematic block diagram showing a fourth embodiment of the present invention.

In the embodiment 3, the first and second multi-way joints are prepared from three-way joints. An embodiment 4 employing four-way joints as multi-way joints is described with reference to FIG. 6. Referring to FIG. 6, members identical to those in FIG. 4 are denoted by the same reference numerals, and hence redundant description is omitted. In this embodiment, four-way joints 26 and 28 are employed as first and second multi-way joints respectively, to divide a channel for a liquid containing no target substance into three. Thus, a second sample solution pipe 25 can be connected through a third three-way joint 27, by employing four-way joints. Thus, it is possible to increase the number of branching of multi-way joints, thereby increasing the number of connectable sample solution pipes.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A concentration measuring device comprising:

a separation mechanism having a porous film possessing a separation function and channels allowing flow of liquids in contact with both surfaces of said film for transferring a target substance between said liquids of said channels through said film;

a first liquid feed channel making a solution containing said target substance flow in one of said channels on first surface of said film of said separation mechanism;

a second liquid feed channel making a liquid containing no said target substance flow in one of said channels on second surface of said film of said separation mechanism; and a detecting part being provided downstream said second surface of said film of said separation mechanism for measuring said target substance, said first liquid feed channel comprising a pipe group at least comprising a plurality of pipes guiding a plurality of solutions containing said target substance respectively, switching mechanisms being provided in intermediate portions of respective said pipes of said pipe group and switching said first liquid feed channel at arbitrary points of time, a joining mechanism being provided downstream said switching mechanisms for joining said pipes with each other, and a liquid feed mechanism being provided downstream said joining mechanism for sucking and discharging liquids, said concentration measuring device further comprising a control unit controlling switching operations of said switching mechanisms and ON/OFF operations of said liquid feed mechanism, said control unit comprising switching mechanism control means making control for closing all said switching mechanisms in advance of measurement, starting suction of said liquid feed mechanism for bringing said pipes into decompressed states, and thereafter opening at least one of said switching mechanisms.

2. The concentration measuring apparatus in accordance with claim 1, wherein said control unit comprises switching mechanism control means making control for superposing times holding open states of said switching mechanism for a pipe of one sample solution being completely measured and said switching mechanism for a pipe of another sample solution at the time of switching one sample solution to another sample solution in measurement and thereafter closing said switching mechanism for said pipe of said one sample solution.

3. The concentration measuring apparatus in accordance with claim 1, wherein said first liquid feed channel includes a plurality of pipes feeding solutions containing said target substance and a pipe feeding a liquid containing no said target substance, and said joining mechanism includes:

a first multi-way joint dividing said pipe feeding said liquid containing no said target substance into channels of the same number as conduits feeding liquids containing said target substance, a three-way joint group set-connecting respective ones of said channels being formed by dividing said pipe feeding said liquid containing no said target substance by said first multi-way joint with respective ones of said pipes feeding liquids containing said target substance in one-to-one relation, and a second multi-way joint set-connecting respective said channels being set-connected by said three-way joint group by pipes of the same length and the same internal diameter for finally connecting the channels into a single pipe.

4. The concentration measuring apparatus in accordance with claim 3, wherein at least single ones of said plurality of pipes feeding said solutions containing said target substance is a standard solution pipe and a sample solution pipe respectively.

5. The concentration measuring apparatus in accordance with claim 4, wherein a fermentation solution is fed in said sample solution pipe as a sample solution.

6. The concentration measuring apparatus in accordance with claim 3, wherein said first multi-way joint for said pipe for said liquid containing no said target substance first dividing said channel in plural in a portion downstream said switching mechanisms with respect to a direction for feeding said liquid is provided at lower position with respect to a horizontal plane than said second multi-way joint finally connecting said set-connected channels into a single pipe.

* * * * *